United States Patent [19]

Maehr

[11] 4,218,560

[45] Aug. 19, 1980

[54] ESTERS OF ANTIBIOTIC X-5108 AND OF MOCIMYCIN

[75] Inventor: Hubert Maehr, Bloomfield, N.J.

[73] Assignee: Hoffmann-La Roche Inc., Nutley, N.J.

[21] Appl. No.: 963,481

[22] Filed: Nov. 24, 1978

Related U.S. Application Data

[63] Continuation of Ser. No. 844,997, Oct. 25, 1977, abandoned.

[51] Int. Cl.$^2$ .................. C07H 7/06; A61K 31/71
[52] U.S. Cl. .................................. 536/1; 424/180; 536/17 R; 536/53
[58] Field of Search .................. 536/17, 1, 53

[56] References Cited

U.S. PATENT DOCUMENTS

| | | | |
|---|---|---|---|
| 2,140,346 | 12/1938 | Bley | 536/120 |
| 2,538,106 | 1/1951 | Kuehl, Jr. | 536/18 |
| 2,949,449 | 8/1960 | Hoffer | 536/4 |
| 4,024,251 | 5/1977 | Maiese et al. | 536/4 |
| 4,062,948 | 12/1977 | Vos et al. | 536/1 |

FOREIGN PATENT DOCUMENTS 7607573  1/1978  Netherlands .................. 536/53

OTHER PUBLICATIONS

Berger et al., "The Jour. of Antibiotics," vol. XXVI, No. 1, 1973, pp. 15-22.

Berger et al., "Chem. Abst.," vol. 78, 1973, pp. 109,258(b).

*Primary Examiner*—Johnnie R. Brown
*Attorney, Agent, or Firm*—Jon S. Saxe; Bernard S. Leon; Frank P. Hoffman

[57] ABSTRACT

Esters of antibiotic X-5108 and of mocimycin, especially the acetic esters, exhibit activity as growth promotants in farm animals.

15 Claims, No Drawings

ESTERS OF ANTIBIOTIC X-5108 AND OF MOCIMYCIN

This is a continuation of application Ser. No. 844,997 filed Oct. 25, 1977 now abandoned.

DESCRIPTION OF THE INVENTION

The present invention relates to ester derivatives of the known antibiotic X-5108 and mocimycin, especially the acetic esters thereof. These esters exhibit activity as growth promotants in farm animals.

The ester derivatives of the present invention have the general formula

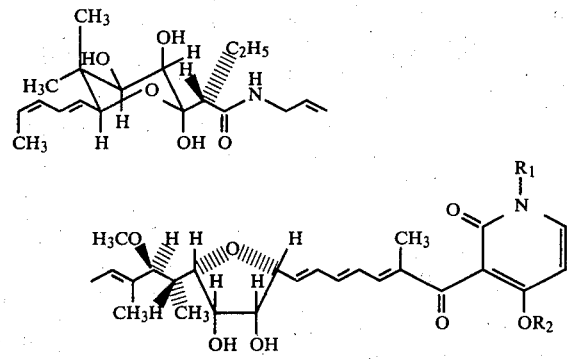

wherein $R_1$ is hydrogen or methyl and $R_2$ is selected from the group consisting of acyl, aroyl and aliphatic or aromatic substituted sulfonyl grouping.

As used in this disclosure, the term "lower alkyl" or "alkyl" comprehends both cyclic, straight or branched-chain ($C_1$–$C_7$) hydrocarbon radicals, preferably $C_1$–$C_4$ hydrocarbon radicals such as methyl, ethyl, propyl, isopropyl, butyl and the like, with methyl as most preferred.

By the term "acyl" as utilized herein, an acyl moiety of a $C_1$–$C_7$ preferably a $C_1$–$C_4$ alkanoic acid is intended, e.g., acetyl, propionyl, butyryl and the like, i.e., moieties of the formula

wherein $R^{20}$ is $C_1$–$C_6$ or hydrogen, or aromatic moieties such as phenylglyoxyloyl derived from benzoylformic acid.

The term "aromatic or aliphatic substituted sulfonyl grouping" comprehends compounds of the formula —$SO_2X$ wherein X is a branched or straight chain $C_1$–$C_7$, preferably $C_1$–$C_4$ aliphatic group e.g., methyl or a substituted or unsubstituted aromatic group such as a phenyl or substituted phenyl derivative e.g., tolyl. Preferred groups include the 4-methylbenzenesulfonyl or 4-acetamidobenzenesulfonyl moieties.

By the term "aroyl" is meant the term

wherein $R^{30}$ is an aromatic group such as benzoyl, naphthoyl, or 3,4,5-trimethoxybenzoyl groups.

By the term "halide" is meant the chloride, bromide or iodide.

The antibiotic X-5108, also known as Goldinodox, or Aurodox, is a starting material in the production of the novel esters of the present invention. Antibiotic X-5108 is obtained by the fermentation of Streptomyces sp. X-5108 as described in U.S. Pat. No. 28,700 to J. Berger. The ester derivatives of the present invention are produced from either antibiotic X-5108 or the mycelial culture in which antibiotic X-5108 is produced. The novel esters of the present invention may also be produced by the utilization of mocimycin as a starting material. The antibiotic mocimycin, also known as kirromycin, is a known compound being the subject of German Pat. No. 2,406,164 and articles by Wolf et al., Tetrahedron Lett., 1973-30, 2823-2826, 1973 and C.A. 77 32742 [1972].

In achieving the subjects of the present invention, in the first step, antibiotic X-5108, preferably in the form of an alkali metal or amine salt thereof, most preferably the sodium, trialkylamine, morpholine, piperidine or pyridine salt, is treated with the acid halide (preferably chloride) or the analogous acid anhydride, if available, of the desired acyl, aroyl or aromatic or aliphatic substituted sulfonyl group, e.g. acetyl, phenylglyoxyloyl, benzoyl, 3,4,5-trimethoxy benzoyl, 4-methylbenzenesulfonyl or 4-acetamido benzenesulfonyl groups. Also the analogous activated ester form of the above groups may be utilized where available e.g., 4-nitrophenyl acetate for the group acetyl.

The above reaction is preferably effected in the presence of an inert organic solvent which is suitable for the purposes of the present invention. Among the many suitable inert organic solvents, there can be included dimethylformamide, hexamethyl phosphoramide, or dimethyl sulfoxide. All that is required of the organic solvent in the above step (as well as in any subsequent steps) is that the starting materials be soluble therein and that the solvent does not interfere with the ensuring reaction. While temperatures and pressure are not critical to a successful performance of the above step, it is preferred to effect the reaction at a temperature range of from about 0° up to about 100°, most preferably at about 5° C. and atmospheric pressure.

The alternate method to provide the novel antibiotic X-5108 esters comprises the initial conversion of mocimycin to its ester, whereby mocimycin is used, preferably in the form of an alkali metal or amine salt thereof, most preferably the sodium salt, and is first treated with the acid halide (preferably chloride) or the analogous acid anhydride of the groups, e.g. acyl, aroyl, etc., as set forth above. Further, the corresponding activated ester may be utilized instead of the acid halide or acid anhydride, along with the reaction conditions described above. The resulting esters of mocimycin are novel and as such represent part of the present invention since they exhibit growth promotant activity.

If it is desirable to produce the esters of antibiotic X-5108 from mocimycin, the mocimycin esters are thereafter N-methylated by utilizing a methyl donor such as methyl halide (preferred is the iodide), dimethyl sulfate or other well known commercially available methyl donors, e.g. methyl trifluoromethanesulfonate or methylfluorosulfonate together with a base which acts as an acid scavenger, such as barium oxide, barium hydroxide or silver oxide, in an inert solvent as set forth above. The temperature of the reaction may range from about 20° C. to about 70° C., most preferably at about room temperature and atmospheric pressure. The reaction is allowed to continue for about 20 minutes to 3 hours, preferably from about 30 minutes to 1.5 hours, most preferably about 70 minutes. The N-methylated product (antibiotic X-5108 esters) may be separated from the reaction mixture utilizing chromatographic methods available to the art, e.g. thin-layer or gel permeation chromatography. It should be stated that removal of the ester at this point leads to X-5108, thus representing the last step in a chemical conversion of mocimycin→X-5108.

The novel esters exhibit growth promotant activity in farm animals, such as, chickens and cattle. The following data represents a measurement of the growth-promoting effects of the novel esters of antibiotic X-5108 as reflected in the testing of a preferred ester. A basal ration was prepared containing the following named ingredients in the quantities hereinafter indicated:

| | Percent by Weight |
|---|---|
| Ground yellow corn | 56.075 |
| Meat and bone meal (50% protein) | 4.000 |
| Fish meal (60% protein) | 4.000 |
| Soybean meal (50% protein) | 28.000 |
| Dehydrated alfalfa meal | 1.000 |
| Animal fat | 4.000 |
| Methionine | 0.200 |
| Rock phosphate | 0.250 |
| Calcium carbonate | 1.200 |
| Iodized salt | 0.250 |
| Vitamin supplement | 1.000 |
| Trace mineral supplement | 0.025 |

As a preferred species, the antibiotics X-5108 acetic ester was added to this ration in a ratio of 50 milligrams of antibiotic per kilogram of ration.

The growth stimulating effects of the ester were determined by allowing poultry to feed, ad libitum, on the antibiotic supplemented ration. In the test, one day old Cornish Cross Sexed Broiler Chicks were used. The test utilized 10 chicks per replicate (5 males and 5 females). The replicate groups were permitted access to the ration. A planned random distribution of the replicates was made to equalize factors of heating, light and position. The birds were observed over a two week period, with group weight being determined several times during the period and individual weights being determined at the end of 14 days. Feed consumption was also recorded and improvement in feed efficiency, as compared to the control, was calculated.

A control experiment was carried out simultaneously, in the manner described as above, except that the chicks which were used in the control test were allowed to feed, ad libitum, on a ration which contained the same nutrient ingredients but did not contain the ester additive.

The average gain for each test group is divided by the average gain of the negative control group and the quotient multiplied by 100 to yield the percent weight gain. Gain is the final body weight of the chick at the end of the 2 week test minus the beginning weight of 1 day of age.

$$\frac{(\text{Av. final wt.} - \text{av. initial wt. of test group})}{(\text{Av. final wt.} - \text{av. initial wt. of control group})} \times 100 = \text{percent wt. gain}$$

The table which follows summarizes the results of the experiment.

TABLE I

| Supplement | Level fed mg/kg | No. of replicates | Beg. Wt. (gr) | End Wt. (gr) | 11-day gain (gr) | % Gain | Feed Conversion | % Improved Feed Conver. |
|---|---|---|---|---|---|---|---|---|
| Basal Control | — | 5 | 50.7 | 146.3 | 95.6 | 0 | 1.888 | 0 |
| Acetic Ester of Antibiotic X-5108* | 20 | 3 | 50.6 | 169.3 | 118.7 | ±24.2 | 1.573 | +20.0 |

*N-[(2E,4E)-7-[[5-(1E,3E,5E)-7-(1,2-Dihydro-4-acetyl-oxy-2-oxo-1-methyl-3-pyridinyl)-6-methyl-7-oxo-1,3,5-heptatrienyl]-tetrahydro-3,4-dihydroxy-2-furanyl]]-6-methoxy-5-methyl-2,4-octadienyl)alpha-ethyl-2,3,4-trihydroxy-5,5-dimethyl-6-[(1E,3Z)-1,3-pentadienyl]-tetrahydro-2H-pyran-2-yl acetamide From the foregoing table it is seen that the chickens fed on the ration supplemented with 20 mg. of antibiotic X-5108 acetic ester per kilogram of feed experienced an increased growth rate as compared to the control. At the same time, as indicated by a 20 percent improvement in feed efficiency, the same birds made more effective use of their feed.

The esters of antibiotic X-5108 and of mocimycin exhibit activity as poultry growth promotants and bring about enhanced feed efficiency in the animals. Thus, in a further embodiment of the present invention, the esters are employed as the active ingredient in new and useful compositions which, upon oral administration to animals, result in an increased growth rate and an enhanced feed efficiency in the animals. Administration of these compositions is accomplished through the production of nutritionally balanced feeds that satisfy the animals' nutrient requirements in addition to supplying the active growth promotant antibiotic X-5108 ester or mocimycin ester.

The growth stimulating compositions of this invention containing as the active ingredient the esters of antibiotic X-5108 or mocimycin are prepared by a variety of methods. Following one such method, the particular ester is added directly to an edible non-toxic carrier. It is preferred that the carrier be a material having nutritional value for poultry; with a high energy poultry feed being the most preferred carrier. In the case where the ester is added directly to the feed, the mixing step can be accomplished by employing known techniques. For example, the nutrient materials which comprise feed are fed, either individually or collectively, into a batch mixer and the antibiotic is then added. The mixer is operated until the product contains a uniform distribution of ingredients throughout.

The nutrient materials used as feeds and for the purpose of this invention as carriers for the esters will vary to some extent depending upon the specific needs of the type of animal being fed and on the final use being made of the animals. However, for the most part these feeds will contain sources of protein, such as fish meal, soybean meal, corn, peanut products and the like; and sources of carbohydrates, such as grains, meals, flours, sugars and the like. In addition, the mineral and vitamin balances for the animals can be maintained by the incorporation into the feed of the required minerals, i.e., sodium, potassium, magnesium, calcium carbonate, etc. and vitamins, i.e., vitamin A, $B_{12}$, D and thiamine. Of course, the feed may also contain other conventional feed additives.

In a preferred method of producing the growth promoting compositions of the invention, the active ingredient is incorporated into a concentrated premix which can then be added to the feed. In preparing the solid form pre-mix containing the esters any suitable carrier or extender material can function as the inert ingredient provided that it be inert to the active antibiotic additive and be non-toxic to the animal receiving the composition. Numerous solid materials satisfy these requirements and, therefore, will function successfully for the purposes of the present invention. Representative of such solid materials are mineral sources such as ground oyster shells, edible cereals, vegetable, marine or animal materials such as are present in commercial animal feeds, corn meal, citrus meal, soybean meal, fish meal, meat scraps, dried fermentation residues and the like.

The novel esters may be blended with one or more of the suitable solid materials discussed above into a mesh, pellet, or any desired configuration by any known and convenient technique. For example, the composition can be formed by finely dividing or pulverizing the active ingredient and the inert ingredients using any commercially available grinder. If the feed material is not present when the grinding or the pulverizing is effected, the resultant material can be distributed in accordance with the present invention in any conveniently available feed material.

The quantity of the esters of antibiotic X-5108 or mocimycin required to achieve the desired growth rate stimulation and feed efficiency enhancement is critical, but may vary within the prescribed rang. Preferably, when used in conjunction with the animal's feed supply, the improved growth promoting composition of the present invention comprises a supplemental animal feed having dispersed therein per 100 parts by weight of feed from about 0.0001 part by weight to about 0.01 part by weight of said active material; namely, the particular antibiotic X-5108 ester or mocimycin esters. Higher concentrations of the ester than 0.01 part by weight per 100 parts by weight of feed do not generally show improved results over the results obtained with 0.01 part per concentration. Thus, it is not advantageous to use amounts greater than 0.01 part by weight of active ingredient per 100 parts by weight of feed. In a preferred embodiment of the invention, the novel growth promoting composition comprises a supplemental poultry feed containing per 100 parts by weight of feed, from about 0.0005 part by weight to about 0.0025 part by weight of the active ingredient.

As indicated above, the preferred practice of the invention invoves initially preparing a concentrated premix containing the active ingredient. Preparation of a premix which can later be added to the feed provides a convenient method of using the growth promoting composition and insures the proper distribution of the active ingredient throughout the feed. The amount of antibiotic X-5108 or mocimycin ester present in the premix is not critical to the operability of the invention. The objectives of the invention are achieved, regardless of the level of antibiotic X-5108 ester or mocimycin ester in the premix, by utilizing a quantity of the premix capable of providing a final feed containing an effective level of the novel antibiotic X-5108 ester or mocimycin ester as defined above. The premix is a convenient manner of supplying the composition to the feed manufacturer or poultry raiser who can then mix suitable amounts of the premix with the available supply of, for example, poultry feed, in order to produce a final feed containing an effective level of the selected ester of antibiotic X-5108 or mocimycin.

The nature and objects of the present invention can be more fully understood by making reference to the following examples. Unless otherwise indicated all temperatures are given in degrees celsius and all parts given are parts by weight.

EXAMPLE 1

Mocimycin phenylglyoxylic ester

Procedure A. Mocimycin sodium salt (500 mg, 0.61 mmol) was dissolved in dimethylformamide (5.5 ml) and 0.7 ml of a solution containing approximately 0.7 mmol of phenylglyoxyloyl chloride, prepared by diluting phenylglyoxyloyl chloride (1 g, 5.93 mmol) with benzene (5 ml), was added. The mixture was kept in the dark overnight and was equilibrated with a mixture of water (10 ml) and chloroform (25 ml). The lower phase was washed consecutively with saturated sodium hydrogencarbonate solution (15 ml) and water (15 ml), concentrated to dryness, redissolved in acetone (2 ml) and chromatographed on a column (50×475 mm) of Sephadex LH-20, packed in acetone and developed with the same solvent. The column effluent was collected in fractions of 10 ml each, and the composition of the fractions was monitored by TLC (System 1*). Compound 1b was eluted as the major band ($R_f$=0.23) essentially free of minor impurities which were eluted immediately before ($R_f$=0.26, 0.30) and after ($R_1$=0.12, 0.16 [unreacted mocimycin], 0.18). Fractions containing pure product were pooled and concentrated to dryness as amorphous, yellow powder with an nmr spectrum similar to that of mocimycin but with additional signals characteristic for the phenylglyoxyloyl group, $\delta_{TMS}^{CDCl_3}$ 3.17 (s, $OCH_3$), 7.47 (m, 3H of phenyl group overlapping with H-6 of pyridone moiety) and 7.95 (d, 2H of phenyl group, $J_o$=8 Hz).

* System 1=chloroform/methanol, 9:1, V/V

Procedure B. Mocimycin (250 mg, 75% purity, 0.235 mmol) was dissolved in anhydrous pyridine (2.5 ml). The solution was cooled in an ice-bath and 0.6 ml of the phenylglyoxyloyl chloride solution described in Procedure A was added under stirring. After 5 min the solution was equilibrated with a mixture of chloroform (25 ml), saturated sodium hydrogen carbonate solution (15 ml) and crushed ice. The chloroform phase was washed twice with ice-cold water, concentrated to dryness, the residue was dissolved in acetone and chromatographed as described previously to yield end product.

EXAMPLE 2

Mocimycin acetic ester

Mocimycin sodium salt (2.10 g, 2.56 mmole) was dissolved in dimethyl formamide (10 ml) and acetic anhydride (0.5 ml) was added. After stirring for 30 minutes, the reaction mixture was quenched by adding it to a stirred mixture of saturated sodium hydrogen carbonate solution (100 ml) and chloroform (75 ml). After 5 minutes of stirring, the resultant mixture was transferred to a separatory funnel containing chloroform (50 ml) and the phases equilibrated. Discarding the aqueous phase, the chloroform phase was washed again with saturated sodium hydrogen carbonate solution. The dried chloroform phase (anhydrous sodium sulfate) was concentrated until most of the dimethylformamide was removed. The residue was dissolved in chloroform (ca 10 ml) and added to petroleum ether (ca 500 ml) to precipitate crude product. The purity of this material depends greatly on the purity of the mocimycin used. Purification of the end product may be achieved by chromatography on a column of Sephadex LH-20 with methanol. NMR $\delta_{TMS}^{CDCl_3}$ 2.12 (s, CH$_3$CO).

EXAMPLE 3

X-5108 phenylglyoxylic ester

A mixture of mocimycin phenylglyoxylic ester (182 mg, 0.196 mmol), silver oxide (approx. 100 mg), dimethyl formamide (9 ml) and methyl iodide (0.37 ml) was shaken for 70 min at room temperature. The suspension was filtered and the filtrate was equilibrated with ethyl acetate (25 ml) and water (50 ml). The ethyl acetate phase was filtered, concentrated to a thin syrup, diluted with acetone (2 ml) and chromatographed on a column (25×450 mm) of Sephadex LH-20 packed in acetone and developed with the same solvent. Fractions containing 5 ml each were collected and analyzed by TLC (System 1), fractions containing the major band ($R_f=0.30$) were largely free of impurities which were eluted immediately before ($R_f=0.33, 0.39, 0.46$) and after ($R_f=0.16, 0.20, 0.25$) and major band. Concentration of the pooled fractions afforded the end product as a yellow, amorphous powder. The nmr spectrum was very similar to that of the mocimycin phenylglyoxylic ester with the exception of a signal for an N-methyl group, $\delta_{TMS}^{CDCl_3}$ 3.17 (s, OCH$_3$), 3.58 (s, N-CH$_3$), 7.39 (d, H-6 of pyridone moiety, $J_o=8$ Hz) overlapping with 7.46 (m, 3H of phenyl group) and 7.96 (d, 2H of phenyl group, $J_o=8$ Hz).

EXAMPLE 4

X-5108 acetic ester

Crude mocimycin acetic ester (182 mg, 0.217 mmole) was methylated and purified as described in Example 3 to yield the acetic ester; NMR $\delta_{TMS}^{CDCl_3}$ 2.12 (s, CH$_3$CO) and 3.53 (s, N-CH$_3$).

EXAMPLE 5

X-5108 phenylglyoxylic ester

X-5108 sodium salt (500 mg, 0.60 mmol) was dissolved in dimethyl formamide and the phenylglyoxyloyl chloride solution (2.5 ml) described in Example 1 was added. The reaction mixture was kept in the dark overnight and was equilibrated with ethyl acetate (100 ml) and water (75 ml). The ethyl acetate phase was washed consecutively with saturated sodium hydrogencarbonate solution (75 ml) and water (75 ml), dried with sodium sulfate, concentrated to a syrup and chromatographed as described in Example 3 to yield antibiotic X-5108 phenylglyoxylic ester.

EXAMPLE 6

X-5108 acetic ester

X-5108 sodium salt (8.6 g, 10.3 mmole) was dissolved in dimethylformamide (100 ml) and acetic anhydride (2.2 ml) was added. After stirring for 30 minutes, the reaction mixture was quenched by adding it to a stirred mixture of saturated sodium hydrogencarbonate solution (250 ml) and chloroform (150 ml). After 20 minutes of stirring the resultant mixture was transferred to a separatory funnel containing chloroform (300 ml) and the phases were equilibrated. Discarding the aqueous phase, the chloroform phase was washed again with saturated sodium hydrogen carbonate solution followed by four water washes. The dried chloroform phase (anhydrous sodium sulfate) was concentrated at 55° C. to a very thick syrupy residue which was dissolved in chloroform (50 ml) and added to petroleum ether (1200 ml) to precipitate crude end product. Purification of the end product may be achieved by chromatography on a column of Sephadex LH-20 with acetone.

EXAMPLE 7

X-5108 Benzoic ester

X-5108 sodium salt (2.2 g; 2.64 mmole) was dissolved in dimethylformamide (25 ml) and cooled in an ice bath. Benzoyl chloride (3 mmole) was added and stirred vigorously for 30 minutes whereupon the reaction mixture was quenched by adding it to a stirred mixture of saturated sodium hydrogen carbonate (100 ml) and chloroform (75 ml). After 20 minutes of stirring the mixture was transferred to a separatory funnel containing chloroform (25 ml) and the phases were equilibrated. Discarding the aqueous phase, the chloroform phase was washed again with saturated sodium hydrogencarbonate solution followed by two water washes. The dried chloroform phase (anhydrous sodium sulfate) was concentrated at 55° C. to a very thick syrup which was dissolved in acetone and purified by chromatography on a column of Sephadex LH-20. The appropriate fractions were pooled and concentrated to the end product.
NMR $\delta_{TMS}^{CDCl_3}$ 3.16 (s, CH$_3$O), 3.57 (s, CH$_3$N), 7.44 (m, 3'-H, 5'-H), 7.60 (m, 4'-H), 7.96 (m, $J_o=8.5$ Hz, 2'-H, 6'-H).

EXAMPLE 8

X-5108 3,4,5-trimethoxybenzoic ester

X-5108 sodium salt (2.2 g; 2.64 mmole) was dissolved in dimethylformamide (25 ml) and cooled in an ice bath. 3,4,5-Trimethoxybenzoyl chloride (3 mmole) was added and stirred vigorously for 30 minutes whereupon the reaction mixture was quenched by adding it to a stirred mixture of saturated sodium hydrogen carbonate (100 ml) and chloroform (75 ml). After 20 minutes of stirring the mixture was transferred to a separatory funnel containing chloroform (25 ml) and the phases were equilibrated. Discarding the aqueous phase, the chloroform phase was washed again with saturated sodium hydrogen carbonate solution followed by two water washes. The dried chloroform phase (anhydrous sodium sulfate) was concentrated at 55° C. to a very thick syrup which was dissolved in acetone and purified by chromatography on a column of Sephadex LH-20. The appropriate fractions were pooled and concentrated to the end product.

NMR $\delta_{TMS}^{CDCl_3}$ 3.17 (s, CH$_3$O), 3.58 (s, CH$_3$N), 3.85, 3.85, 3.90 (s, 3 CH$_3$O-C≦), 7.21 (s, 2'-H, 6'-H).

EXAMPLE 9

X-5108 4-methylbenzenesulfonic ester

X-5108 sodium salt (2.2 g; 2.64 mmole) was dissolved in dimethylformamide (25 ml) and cooled in an ice bath. 4-methyl benzene sulfonyl chloride (3 mmole) was added and stirred vigorously for 30 minutes whereupon the reaction mixture was quenched by adding it to a stirred mixture of saturated sodium hydrogen carbonate (100 ml) and chloroform (75 ml). After 20 minutes of stirring the mixture was transferred to a separatory funnel containing chloroform (25 ml) and the phases were equilibrated. Discarding the aqueous phase, the chloroform phase was washed again with saturated sodium hydrogen carbonate solution followed by two water washes. The dried chloroform phase (anhydrous sodium sulfate) was concentrated at 55° C. to a very thick syrup which was dissolved in acetone and purified by chromatography on a column of Sephadex LH-20. The appropriate fractions were pooled and concentrated to the end product.

NMR $\delta_{TMS}^{CDCl_3}$ 2.40 (s, C$\underline{H}_3$C$_6$H$_4$), 3.14 (s, CH$_3$O), 3.49 (s, CH$_3$N), 7.26, 7.65 (AA'BB', J$_o$=8.5 Hz, C$_6$H$_4$ aromatic).

EXAMPLE 10

X-5108 4-acetamidobenzenesulfonic ester

X-5108 sodium salt (2.2 g; 2.64 mmole) was dissolved in dimethylformamide (25 ml) and cooled in an ice bath. 4-Acetamido benzene sulfonyl chloride (3 mmole) was added and stirred vigorously for 30 minutes whereupon the reaction mixture was quenched by adding it to a stirred mixture of saturated sodium hydrogen carbonate (100 ml) and chloroform (75 ml). After 20 minutes of stirring the mixture was transferred to a separatory funnel containing chloroform (25 ml) and the phases were equilibrated. Discarding the aqueous phase, the chloroform phase was washed with saturated sodium hydrogencarbonate solution followed by two water washes. The dried chloroform phase (anhydrous sodium sulfate) was concentrated at 55° C. to a very thick syrup which was dissolved in acetone and purified by chromatography on a column of Sephades LH-20. The appropriate fractions were pooled and concentrated to the end product.

NMR $\delta_{TMS}^{CDCl_3+DMSO}$ 2.17 (s, CH$_3$CO), 3.17 (s,CH$_3$O), 3.51 (s, CH$_3$N), 7.68, 7.76 (AA'BB',J$_o$=9 Hz, C$_6$H$_4$ aromatic), 9.53 (s, NHCO).

What is claimed is:

1. A compound of the formula

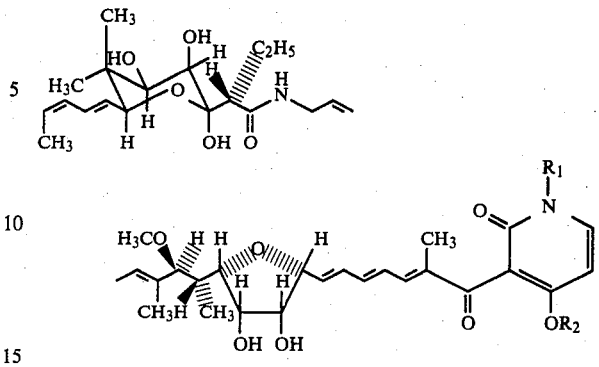

wherein R$_1$ is hydrogen or methyl and R$_2$ is selected from the group consisting of an acyl moiety of a C$_1$ to C$_7$ alkanoic acid, the group

wherein R$^{30}$ is selected from the group consisting of benzoyl, napthoyl and 3,4,5-trimethoxybenzyl and a compound of the formula -SO$_2$X wherein X is selected from the group consisting of a C$_1$ to C$_7$ branched or straight chain alkyl, phenyl and tolyl.

2. The compound of claim 1 wherein R$_1$ is hydrogen and R$_2$ is an acyl moiety of a C$_1$ to C$_7$ alkanoic acid.

3. The compound of claim 2 wherein R$_2$ is acetyl.

4. The compound of claim 1 wherein R$_1$ is methyl and R$_2$ is an acyl moiety of a C$_1$ to C$_7$ alkanoic acid.

5. The compound of claim 4 wherein R$_2$ is acetyl.

6. The compound of claim 1 wherein R$_1$ is hydrogen and R$_2$ is selected from the group consisting of benzoyl, naphthoyl and 3,4,5-trimethoxybenzoyl.

7. The compound of claim 1 wherein R$_1$ is methyl and R$_2$ is selected from the group consisting of benzoyl, naphthoyl and 3,4,5-trimethoxybenzoyl.

8. The compound of claim 1 wherein R$_2$ is a compound of the formula -SO$_2$X wherein X is selected from the group consisting of a C$_1$ to C$_7$ branched or straight chain alkyl, phenyl and tolyl.

9. The compound of claim 8 wherein R$_2$ is a compound of the formula -SO$_2$X wherein X is phenyl or tolyl.

10. The acetic ester of mocimycin.
11. The acetic ester of X-5108.
12. The benzoic ester of X-5108.
13. The 3,4,5-trimethoxybenzoic ester of X-5108.
14. The 4-methylbenzenesulfonic ester of X-5108.
15. The 4-acetamidobenzenesulfonic ester of X-5108.

* * * * *